US011877998B2

(12) United States Patent
Torok et al.

(10) Patent No.: US 11,877,998 B2
(45) Date of Patent: Jan. 23, 2024

(54) SUPPLEMENT COMPOSITION

(71) Applicant: H & H SCIENCE, LLC, Medina, OH (US)

(72) Inventors: Helen M. Torok, Medina, OH (US); Heather L Funk, Medina, OH (US)

(73) Assignee: H &H Science, LLC, Medina, OH (US)

( * ) Notice: Subject to any disclaimer, the term of this patent is extended or adjusted under 35 U.S.C. 154(b) by 203 days.

(21) Appl. No.: 16/564,770

(22) Filed: Sep. 9, 2019

(65) Prior Publication Data

US 2019/0388390 A1  Dec. 26, 2019

Related U.S. Application Data

(63) Continuation-in-part of application No. 15/644,158, filed on Jul. 7, 2017, now abandoned.

(51) Int. Cl.

| | |
|---|---|
| *A61P 17/00* | (2006.01) |
| *A61K 9/48* | (2006.01) |
| *A61K 31/375* | (2006.01) |
| *A61K 31/07* | (2006.01) |
| *A61K 31/355* | (2006.01) |
| *A61K 31/4415* | (2006.01) |
| *A61K 33/30* | (2006.01) |
| *A61K 33/34* | (2006.01) |
| *A61K 36/738* | (2006.01) |
| *A23L 33/16* | (2016.01) |
| *A61K 31/455* | (2006.01) |
| *A61K 9/00* | (2006.01) |
| *A23L 33/155* | (2016.01) |
| *A23L 33/24* | (2016.01) |
| *A61K 47/12* | (2006.01) |
| *A61K 47/38* | (2006.01) |

(52) U.S. Cl.
CPC .......... *A61K 31/375* (2013.01); *A23L 33/155* (2016.08); *A23L 33/16* (2016.08); *A23L 33/24* (2016.08); *A61K 9/0053* (2013.01); *A61K 9/48* (2013.01); *A61K 31/07* (2013.01); *A61K 31/355* (2013.01); *A61K 31/4415* (2013.01); *A61K 31/455* (2013.01); *A61K 33/30* (2013.01); *A61K 33/34* (2013.01); *A61K 36/738* (2013.01); *A61K 47/12* (2013.01); *A61K 47/38* (2013.01)

(58) Field of Classification Search
None
See application file for complete search history.

(56) References Cited

U.S. PATENT DOCUMENTS 5,962,517 A * 10/1999 Murad ................. A61K 31/555
514/474
2012/0121725 A1* 5/2012 Garnier ................. A61Q 19/00
424/638

FOREIGN PATENT DOCUMENTS

CA       2680502 A1 *  4/2011  ............. A61K 31/51

OTHER PUBLICATIONS

Keri JE. Acne: improving skin and self-esteem. Pediatric annals. Mar. 1, 2006;35(3):174-9. (Year: 2006).*
Nybom H, Werlemark G. Beauty is as beauty does-Culinary and medicinal use of rosehips. InVI International Symposium on Rose Research and Cultivation 1064 Aug. 25, 2013 (pp. 137-150). (Year: 2013).*
"What Are the Benefits of Rosehip Oil?"; https://www.healthline.com/health/rosehip-oil-benefits#risk-factors, accessed Jul. 20, 2021 (Year: 2021).*
Vitamin E Fact Sheet for Medical Professionals, updated Mar. 26, 2021 from https://ods.od.nih.gov/factsheets/Vitamin E-Health Professional/ (Year: 2021).*
Shalita AR, Falcon R, Olansky A, Iannotta P, Akhavan A, Day D, Janiga A, Singri P, Kallal JE. Inflammatory acne management with a novel prescription dietary supplement. Journal of drugs in dermatology: JDD. Dec. 1, 2012;11(12):1428-33. (Year: 2012).*
NicAzel label information, revised Feb. 2015 (Year: 2015).*

* cited by examiner

*Primary Examiner* — Nissa M Westerberg
(74) *Attorney, Agent, or Firm* — Tucker Ellis LLP; Michael G. Craig

(57) ABSTRACT

One or more techniques and/or systems are disclosed for a method of administering a composition of an orally administered agent devised to provide desirable nutrients and other supplements to the body, which may help mitigate degradation of the skin, and may help promote the health of the skin, and/or treatment of skin conditions. The composition can comprise ingredients of a selected type, amount, and source, which, in this particular arrangement, may promote healthy skin and improve skin condition in a person. A composition that promotes healthy skin can comprise vitamin A; vitamin C; vitamin E; vitamin B6; zinc; rose hip extract; copper; and vitamin B3.

19 Claims, No Drawings

SUPPLEMENT COMPOSITION

This application is a continuation-in-part application of U.S. Ser. No. 15/644,158, entitled CLEAR SKIN VITAMIN, filed Jul. 7, 2017, which is incorporated herein by reference.

BACKGROUND

The skin is the largest human organ and comprises the dermal layer and the epidermis layer. The skin acts as a barrier against environmental exposure, and a transport barrier between the inside and outside of the body. The skin changes as the body ages and is exposed to certain environmental conditions or contaminants. Internal deterioration may also occur, resulting from regeneration slowdown, free radicals, oxidation, and loss of certain constituents. Changes to the skin may be mitigated through proper care and diet.

SUMMARY

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

A composition of an orally administered agent may be devised to provide desirable nutrients and other supplements to the body, which may help mitigate degradation of the skin, and may help promote the health of the skin. The composition can comprise ingredients in a new arrangement of type, amount, and source, which, in this particular arrangement, may promote healthy skin and improve skin condition in a person.

In one implementation, a composition that promotes healthy skin can comprise the following ingredients: vitamin A; vitamin C; vitamin E; vitamin B6; zinc; rose hip extract; copper; and vitamin B3. The composition can be administered orally at a desired dosage to achieve a desired treatment result, such as to improve skin condition, and/or treat skin conditions.

To the accomplishment of the foregoing and related ends, the following description and annexed drawings set forth certain illustrative aspects and implementations. These are indicative of but a few of the various ways in which one or more aspects may be employed. Other aspects, advantages and novel features of the disclosure will become apparent from the following detailed description when considered in conjunction with the annexed drawings.

DETAILED DESCRIPTION

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are shown in block diagram form in order to facilitate describing the claimed subject matter.

A composition may be devised that can be taken orally by a subject to promote and support healthy skin, including, but not limited to, treating and improving an acne condition in a person. When choosing ingredients for an oral supplement taken by a subject, the ingredients can be selected to devise a formula that is clean, effective for the purpose, and safe for use by humans. The active ingredients of this oral supplement were selected based on this premise.

In one implementation a composition to improve skin health, including improving a skin acne condition, can comprise vitamin A, which is a useful ingredient in treating acne, and is also an anti-inflammatory. In this implementation, a dose from approximately two-thousand (2000) international units (IU) to about three-thousand (3000) IU per day may be effective, and is not likely to cause side effects. Over consumption of vitamin A may result in headaches, and be teratogenic. Further, vitamin C may be included as a natural anti-inflammatory agent, and may also help to reduce skin redness. As an example, a dose from approximately one-hundred and fifty (100) milligrams (mg) to about two-hundred (200) mg per day can be effective without causing side effects. For example, an overdose of vitamin C may result in kidney stones. Additionally, vitamin E can be include, which may help both the vitamin. A and vitamin C be more effective, and provide for better absorption of both. As an example, a dose of approximately forty (40) IU to about sixty (60) IU per day can be very effective.

In this implementation, the composition may also comprise vitamin B3, which can help block male hormone receptors in the skin; and is also effective to help block new acne lesions, and mitigating acne lesions. Vitamin B3 can also help post-inflammatory inflammation heal faster, which may result in less scarring. As an example, a dose from approximately four-hundred (400) mg to about six-hundred (600) mg per day may be effective. An overdose of vitamin B3 may result in skin flushing. Further, in this implementation, vitamin B6 may also provide for facilitation of male hormone receptor blocking in the skin, and can thus help vitamin B3 in its prevention of acne lesions. As an example, a dose from approximately thirty (30) to about fifty (50) mg per day may be effective.

In this implementation, the composition may also comprise Zinc. Zinc can provide natural healing properties; and may promote quicker onset of healing, which can result in less scarring, and may prevent some acne. As an example, a dose from approximately twenty (20) mg to about sixty (60) mg per day may be sufficient to provide efficacy. Further, in this implementation, copper, like zinc, is an elemental natural ingredient that can be very effective in clearing and healing acne; and may provide supplemental benefits in combination with zinc. As an example, a dose from approximately one (1) mg to about three (3) mg per day may be effective. Additionally, rose hip extract may be able to provide natural anti-inflammatory benefits, similar to that of vitamin C. As an example, a dose from approximately five (5) mg to about fifteen (15) mg per day may be effective.

In one implementation, the composition may be disposed in a capsule to be provided as an oral supplement capable of being effectively consumed by a subject, which is taken orally. In one implementation, the capsule may comprise a gelatin-based capsule. In another implementation, the capsule may comprise a vegetable-based capsule, for example, comprising hypromellose. In one implementation, the capsule may comprise a size that is selected to appropriately house the composition. As an example, capsule sizes typically include 000, 00, 0, 1, 2, 3, 4, and 5. In one implementation, the capsule size can comprise size 00. Additionally, in one implementation, the combined weight of the composition and the capsule may comprise from approximately seven-hundred (700) mg to about nine-hundred (900) mg.

As one example, a desired combined weight may comprise from approximately seven-hundred and sixty (760) mg to about eight-hundred and forty (840) mg.

In one implementation, the composition can be disposed in a capsule that is configured to disintegrate or dissolve in the subject (e.g., in the digestive tract of a person) within a desired time. As an example, the capsule may be configured to disintegrate from about five (5) minutes to about sixty (60) minutes in the subject. As another example, the desired time may comprise approximately thirty minutes. In one implementation, the capsule may also comprise an encapsulate or coating that facilitates provision of the desired disintegration time. That is, for example, the encapsulate may coat the capsule to increase (e.g., or decrease) the disintegration time in the digestive tract.

In one implementation, the active ingredients of the composition (as a preferred implementation) can comprise the following approximate composition and amounts:

Vitamin A (as retinyl acetate): 2500 International Units (IU);
Vitamin C (as ascorbic acid): 150 milligrams (mg);
Vitamin E (as dl-alpha-tocopheryl acetate): 50 IU;
Vitamin B6 (as pyridoxine HC1): 40 mg;
Zinc (as zinc gluconate): 40 mg;
Rose hip extract (as a rose hip fruit powder): 10 mg;
Copper (as cupric oxide): 2 mg;
Vitamin B3 (as niacinamide): 500 mg.

In one implementation, the oral supplement may comprise one or more inactive ingredients or excipients. As an example, an inactive ingredient may be used to provide desired characteristics to the supplement that are not typically related to the target treatment, health support, or overall therapeutic characteristics of the active ingredients. For example, inactive ingredients may support binding, act as a dye, preservative, and/or flavoring agent. In one implementation, the oral supplement may comprise one or more inactive ingredients, including one or more of: microcrystalline cellulose and magnesium stearate.

In one aspect, vitamin A can be used for treatment of certain skin conditions, including, but not limited to: acne, eczema, psoriasis, cold sores, wounds, burns, sunburn, keratosis follicularis (Darter's disease), ichthyosis (noninflammatory skin scaling), lichen planus pigmentosus, and pityriasis rubra pilaris. As an illustrative example, a study published in acta dermato-venereologica in 1978 by French researchers described some of the benefits of combining oral use of vitamin A with oral use of zinc. Further, the study results showed that taking zinc along with oral vitamin A can result in a significant increase in the serum levels of retinol-binding proteins (RBPs). RBPs are said to be responsible for the transport and distribution of bioactive vitamin A to organs, such as the skin, in acne patients after four weeks. The study revealed that this effect was not observed in study participants who took only zinc or only took oral vitamin A. Oral vitamin A dosage forms may be an improved use of the vitamin in treating acne. As an example, because no one vitamin can "cure" acne, it may be beneficial to take vitamin A, to treat acne, as part of a combination of other supplements that are effective in acne treatment.

Further in one aspect, vitamin C can aid in skin care because of its antioxidant properties, and because of its importance in collagen synthesis. For example, taking vitamin c orally may be able to enhance the effectiveness of sunscreens applied to the user's skin, for improved protection from the sun's harmful UV rays. Vitamin C may facilitate in decreasing cell damage and helping the healing process of bodily wounds. Further, Vitamin C may also help fend off the signs of aging because of its vital role in the body's natural collagen synthesis. For example, collagen can help to heal damaged skin and, in some cases, can reduce the appearance of wrinkles.

Additionally, in one aspect, orally ingested vitamin E may be used to help treat erythema; a redness of the skin resulting from a congestion of capillaries in the skin. Further, vitamin E may assist in additional sun protection for the skin, for example, as supplementation with vitamin E has been shown to reduce photodamage, wrinkles and potentially improve skin texture. Vitamin E is also an integral part of the skin's antioxidant defenses, primarily providing protection against UV radiation and other free radicals that may be exposed to the epidermis. As one example, studies have noted that oral supplementation with only vitamin E may not provide adequate protection for the skin; and supplementing vitamin E with vitamin C may be able to effectively increase the photoprotection of skin. For example, vitamin E can act as a radical scavenger, disabling production of damaging free radicals in tissues by reacting with them to form a tocopheryl radical, which can then be reduced by a hydrogen donor, such as vitamin C, and returned to a reduced state. This powerful antioxidant activity may be able to help reduce free radical damage that leads to fine lines in the skin. A study also found that men who took vitamin E supplements grew more hair than those given a placebo. Further, as one example, vitamin E gel cap form may be more effective, as vitamin E is fat-soluble.

Vitamin B6 may be helpful for the treatment of Atopic eczema, a skin disorder that can cause itchy, scaly rashes. As an example, early studies are looking into the supplementation with vitamin B6 for the treatment of atopic eczema. These early study have yet to find convincing evidence of an effect; and high-quality research is needed to make firm conclusions.

Zinc may be used to treat acne, amongst other things. Many acne sufferers have been shown to be deficient in zinc, and their acne often improves when they start supplementing with oral zinc. Zinc is a trace mineral essential to all forms of life because of its fundamental role in gene expression, cell growth and cell replication. While the exact mechanisms are unknown, zinc most likely promotes healthy skin by carrying vitamin A to the skin, and by regulating the body's hormonal balance. Zinc may also be important to the absorption, transport and usage of vitamin A in the body. Therefore, zinc deficiency also result in vitamin A deficiency. Further, studies have found that zinc facilitates apoptosis, or programmed cell death, which is a natural part of the skin renewing itself. For example, if apoptosis is delayed, such as due to zinc deficiency, skin cells may stick together instead of dying and sloughing off, which can lead to clogged pores.

Zinc also exhibit anti-inflammatory properties, and is commonly used to treat a variety of many common inflammatory dermatoses, such as acne, rosacea, eczemas, and ulcers and wounds of varied etiology. Acne vulgaris is a common disorder among the adolescent age group affecting 90-95% of the mid-teen population. A large variety of topical and systemic agents are often used for management of acne vulgaris, including the use of oral and topical antibiotics and/or retinoids. For example, a chronic persistent clinical course of these products for treatment of acne, along with the emergence of resistance to common antibiotics, has led to trial of numerous novel agents in acne management. As one example, zinc has been used both topically and systemically for the management of acne vulgaris since its favorable effect on acne was recognized. Zinc can have an anti-inflammatory affect, which may calm irritated or broken-out skin. Further, zinc can help regulate cell production and turnover, and can help reduce the amount of natural oil the skin produces.

Rose hip is the fruit of the rose plant, including the Dog Rose, or Rosa canina. This rose grows mostly in Europe and parts of Africa and Asia. Rose hips are known to be good sources of vitamin C and other antioxidants, vitamins, and minerals. Rose hips may also contain a substance that fights inflammation. There is evidence that suggests that rose hips can also help with skin integrity, for example, as rose hip contains anti-inflammatory and anti-swelling properties. Rose hip oil contains healthy fatty acids that may help keep the skin healthy and plump. Further, rose hip may also fight against free radical damage, and helps people with acne problems, including the reduction of the appearance of acne scars.

Copper is also an essential mineral for the body. Copper is known to contribute to skin and hair health by helping the body make melanin, which helps protect the skin from the UV rays. Zinc and copper work together and separately to control metabolism. Both minerals help activate the enzyme copper-zinc superoxide dismutase, which provides antioxidant activity for the body.

Vitamin B3, such as oral or topical niacinamide, has been shown to reduce UV-induced immunosuppression. For example, oral niacinamide can reduce the onset of actinic keratosis, a pre-cancerous area of thick or scaly skin; indicating that this vitamin may be helpful in reducing more terminal forms of photoaging. Further, studies have found that oral niacin may reduce nonmelanoma skin cancer by a quarter in a high risk group. Additionally, some research has demonstrated that oral niacinamide may improve melasma and vitiligo conditions.

In one aspect, the composition that promotes healthy skin, described herein, is improved over existing formulations and oral supplements, as it does not need a prescription, is more affordable, and is comprised of more available ingredients. For example, existing supplements do not have the same amounts or types of vitamin B6 and vitamin A. Further, some existing acne treatment supplements require a prescription, and it can be difficult to get insurance coverage of a supplement. Insurance companies typically want supplements to be over the counter, and not be provided as a prescription. Therefore, to provide appropriate types and amounts of vitamins B6, C, A, and copper and zinc to provide more efficacy for acne treatment, using materials and sources that could be made affordable and readily available manner, research revealed the current composition that is not available in other acne therapeutic supplements. Additionally, for example, the combination of vitamin B6 and vitamin B3 (e.g., as Niacinamide), along with the inclusion of the vitamin A, C and E potentiates, can further improvise the benefits of vitamin B3 (e.g., as Niacinamide). For example, this combination may causes quicker onset of effective action, and provide for improved absorption by the skin.

In this aspect, the current composition has been identified as easily tolerated by the digestive system. Further, the current composition has a quick onset of action with results that can be evident within the first month of use. Additionally, the current composition, at the type and amounts described, may mitigate allergic reactions in the typical population. As an example, the oral supplement, as described, may be provide effective benefit for both males and females. The supplement may also mitigate potential cross reactions with other medications, such as oral contraceptives.

In one aspect, a method for promoting skin health can be devised. In one implementation, in this aspect, promoting skin health can comprise treatment and prevention of an acne condition associated with a subject's skin. Further, promoting skin health can comprising delaying onset of signs and conditions associated with aging skin; healing skin conditions; and/or therapeutic treatment of other skin conditions. In one implementation, in this aspect, the method can comprise administering an oral supplement to a subject, where the oral supplement comprises an effective amount of a composition that promotes skin health. As an example, the composition may comprise one or more portions of one or more of the formulations described herein.

In one implementation, the composition utilized by the method can comprise: vitamin A; vitamin C; vitamin E; vitamin B6; zinc; rose hip extract; copper; and vitamin B3. Further, in one implementation, the composition can comprise the specified ingredients in desired amounts, such as: vitamin A (e.g., as retinyl acetate) of about 2000 IU to about 3000 IU; vitamin C (e.g., as ascorbic acid) from about 100 mg to about 200 mg; vitamin E (e.g., as dl-alpha-tocopheryl acetate) from about 40 IU to about 60 IU; vitamin B6 (e.g., as pyridoxine HCl) from about 30 mg to about 50 mg; zinc (e.g., as zinc gluconate) from about 20 mg to about 60 mg; rose hip extract (e.g., as a rose hip fruit powder) from about 5 mg to about 15 mg; copper (e.g., as cupric oxide) from about 1 mg to about 3 mg; and vitamin B3 (e.g., as niacinamide) from about 400 mg to about 600 mg.

Further, in one implementation, the supplement used in this method, in this aspect, can comprise a weight of from 700 mg to about 900 mg. Additionally, in one implementation, the composition, and/or supplement, can comprise one or more inactive ingredients. For example, the inactive ingredients can comprise one or more of microcrystalline cellulose, and magnesium stearate. In one implementation of this method, the administration of the oral supplement can comprise the subject taking (e.g., consuming) one or two capsules, comprising the supplement, on a daily basis.

In one implementation, a method of treating a subject with a history of actinic keratosis, or solar keratosis, damage may utilize one or more of the supplement compositions described herein. Actinic damage may be diagnosed by a rough, crusty, scaly growth on the dermis, which can be a result of exposure to UV radiation. In this implementation, treating a subject with a history of actinic or solar keratosis can comprise orally administering 2 capsules of the supplement composition per day, for ongoing repair of the skin.

In one implementation, a method of treating or supplementing skin health for those with a history of basal cell carcinoma and/or squamous cell carcinoma may utilize one or more of the supplement compositions described herein. Basal cell carcinoma is diagnosed as a type of skin cancer that appears as a white waxy lump or a brown scaly patch. Squamous cell carcinoma is diagnosed as a type of cancer that appears as firm, red nodules or open sores. In this implementation, treating a subject having a history of basal cell carcinoma and/or squamous cell carcinoma can comprise orally administering 2 capsules of the supplement composition per day, for ongoing repair of the skin.

In one implementation, a method of treating a subject having a history of melanoma may utilize one or more of the supplement compositions described herein. Melanoma is diagnosed as a type of cancer that appears as hyper pigmented irregular patches. In this implementation, treating a subject that has a history of melanoma can comprise orally administering 2 capsules of the supplement composition per day, for ongoing repair of the skin.

In one implementation, a method of treating melasma may utilize one or more of the supplement compositions described herein. Melasma is diagnosis by an appearance of gray-brown patches on the face, often corresponding to hormonal changes, such as during pregnancy. In this implementation, treating melasma can comprise orally administering 2 capsules of the supplement composition per day for substantially clear skin in within three months.

In one implementation, a method of treating acne may utilize one or more of the supplement compositions described herein. Acne can be occur when pores become plugged with oil and dead skin cells, resulting in uninflamed blackheads, or large, red, tender bumps. In this implementation, treating acne can comprise orally administering 2 capsules of the supplement composition per day for substantially clear skin in within two months.

In one implementation, a method of treating Rosacea may utilize one or more of the supplement compositions described herein. A rosacea diagnosis can be indicated by the appearance of flushed redness with bumps and visible blood vessels on the face. In this implementation, treating rosacea can comprise orally administering 2 capsules of the supplement composition per day for substantially clear skin in within two months.

In one implementation, a method of treating psoriasis may utilize one or more of the supplement compositions described herein. A diagnosis of psoriasis can indicate the appearance of red, scaly, dry patches that are often itchy. In this implementation, treating psoriasis can comprise orally administering 2 capsules of the supplement composition per day for continued improvement, for ongoing repair of the skin, and/or at least until the appearance of the psoriasis is reduced or eliminated.

In one implementation, a method of treating vitiligo may utilize one or more of the supplement compositions described herein. A diagnosis of vitiligo indicates a loss of natural skin color at an unpredictable rate, often appearing bleached. In this implementation, treating vitiligo can comprise orally administering 2 capsules of the supplement composition per day for continued improvement over one year, for ongoing repair of the skin, and/or at least until the appearance of the vitiligo is reduced or eliminated.

In one implementation, a method of treating atopic dermatitis, or eczema, may utilize one or more of the supplement compositions described herein. A diagnosis of atopic dermatitis indicates red skin is red that is itchy and often appearing in periodic flares. In this implementation, treating atopic dermatitis or eczema can comprise orally administering 2 capsules of the supplement composition per day for continued improvement, for ongoing repair of the skin, and/or at least until the appearance of the atopic dermatitis, or eczema is reduced or eliminated.

In one implementation, a method of treating perioral dermatitis may utilize one or more of the supplement compositions described herein. Perioral dermatitis can be diagnosed by the appearance of a rash that is red, with scaly bumps often around the mouth and nose. In this implementation, treating perioral dermatitis can comprise orally administering 2 capsules of the supplement composition per day for substantially clear skin in within one month.

In one implementation, a method of treating skin ulcers and wounds may utilize one or more of the supplement compositions described herein. Skin ulcers and wounds can be diagnosed by open sores often caused by poor blood flow for an extended period of time. In this implementation, treating skin ulcers/wounds can comprise orally administering 2 capsules of the supplement composition per day for substantially clear skin in within four to six months.

In another implementation, for respective diagnosis of skin conditions, and/or for intense skin exposure in winter or summer, three or more capsules of the supplement can be administered orally per day at least until the skin condition is mitigated, and/or the environmental cause for the condition has been mitigated.

In another implementation, for example, where the underlying symptoms or expressions of a skin condition are less severe, and/or for ongoing promotion of skin health, one capsule of the supplement can be administered orally per day at least until the skin condition is mitigated.

Moreover, the word "exemplary" is used herein to mean serving as an example, instance or illustration. Any aspect or design described herein as "exemplary" is not necessarily to be construed as advantageous over other aspects or designs. Rather, use of the word exemplary is intended to present concepts in a concrete fashion. As used in this application, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Further, At least one of A and B and/or the like generally means A or B or both A and B. In addition, the articles "a" and "an" as used in this application and the appended claims may generally be construed to mean "one or more" unless specified otherwise or clear from context to be directed to a singular form.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes," "having," "has," "with," or variants thereof are used in either the detailed description or the claims, such terms are intended to be inclusive in a manner similar to the term "comprising."

The implementations have been described, hereinabove. It will be apparent to those skilled in the art that the above methods and apparatuses may incorporate changes and modifications without departing from the general scope of this invention. It is intended to include all such modifications and alterations in so far as they come within the scope of the appended claims or the equivalents thereof.

What is claimed is:

1. A method for treating a skin condition, comprising:
orally administering an effective amount of an oral supplement to a subject, the oral supplement comprising:
a capsule holding a composition, wherein one capsule of the composition comprising a weight of from 700 mg to about 900 mg:
the composition, comprising:
vitamin A;
vitamin C;
vitamin E in the form of dl-alpha-tocopheryl acetate of about 40 IU to about 60 IU;
vitamin B6;
zinc in the form of zinc gluconate of about 20 mg to about 60 mg;
rose hip extract;
copper; and
vitamin B3.

2. The method of claim 1, the composition comprising:
vitamin A in the form of retinyl acetate of about 2000 IU to about 3000 IU;
vitamin C in the form of ascorbic acid of about 100 mg to about 200 mg;
vitamin B6 in the form of pyridoxine HCl of about 30 mg to about 50 mg;
rose hip extract in the form of a rose hip fruit powder of about 5 mg to about 15 mg;
copper in the form of cupric oxide of about 1 mg to about 3 mg; and
vitamin B3 in the form of niacinamide of about 400 mg to about 600 mg.

3. The method of claim 1, the composition comprising one or more of:
microcrystalline cellulose as an inactive ingredient; and
magnesium stearate as an inactive ingredient.

4. The method of claim 1, the administering comprising orally consuming at least one capsule of the oral supplement on a daily basis.

5. The method of claim 1, comprising treating a subject having actinic or solar keratosis by administering at least two capsules of the oral supplement on a daily basis.

6. The method of claim 1, comprising treating a subject having a history of basal cell carcinoma or squamous cell carcinoma by administering at least two capsules of the oral supplement on a daily basis.

7. The method of claim 1, comprising treating a subject having a history of melanoma by administering at least two capsules of the oral supplement on a daily basis.

8. The method of claim 1, comprising treating a subject having melasma by administering at least two capsules of the oral supplement on a daily basis.

9. The method of claim 8, comprising administering at least two capsules of the oral supplement on a daily basis for up to three months.

10. The method of claim 1, comprising treating a subject having acne by administering at least two capsules of the oral supplement on a daily basis.

11. The method of claim 10, comprising administering at least two capsules of the oral supplement on a daily basis for up to two months.

12. The method of claim 1, comprising treating a subject having rosacea by administering at least two capsules of the oral supplement on a daily basis.

13. The method of claim 12, comprising administering at least two capsules of the oral supplement on a daily basis for up to two months.

14. The method of claim 1, comprising treating a subject having psoriasis by administering at least two capsules of the oral supplement on a daily basis.

15. The method of claim 1, comprising treating a subject having vitiligo by administering at least two capsules of the oral supplement on a daily basis.

16. The method of claim 1, comprising treating a subject having atopic dermatitis by administering at least two capsules of the oral supplement on a daily basis.

17. The method of claim 1, comprising treating a subject having perioral dermatitis by administering at least two capsules of the oral supplement on a daily basis.

18. The method of claim 17, comprising administering at least two capsules of the oral supplement on a daily basis for up to one month.

19. The method of claim 1, comprising treating a subject having skin ulcers by administering at least two capsules of the oral supplement on a daily basis.

* * * * *